(12) United States Patent
Casey et al.

(10) Patent No.: US 11,406,403 B2
(45) Date of Patent: Aug. 9, 2022

(54) VISIBILITY OF MECHANICAL THROMBECTOMY DEVICE DURING DIAGNOSTIC IMAGING

(71) Applicant: Neuravi Limited, Galway (IE)

(72) Inventors: Brendan Casey, Galway (IE);
Jacqueline O'Gorman, Clare (IE);
David Vale, Galway (IE)

(73) Assignee: Neuravi Limited, Galway (IE)

( * ) Notice: Subject to any disclaimer, the term of this patent is extended or adjusted under 35 U.S.C. 154(b) by 272 days.

(21) Appl. No.: 16/441,537

(22) Filed: Jun. 14, 2019

(65) Prior Publication Data
US 2020/0390459 A1 Dec. 17, 2020

(51) Int. Cl.
*A61B 17/221* (2006.01)
*A61B 90/00* (2016.01)

(52) U.S. Cl.
CPC .... *A61B 17/221* (2013.01); *A61B 2017/2212* (2013.01); *A61B 2090/3966* (2016.02)

(58) Field of Classification Search
CPC .......... A61B 17/221; A61B 2017/2212; A61B 2017/2215; A61B 2017/2217; A61B 17/22031; A61B 2017/22034; A61B 2017/22035; A61B 90/39; A61B 2090/3966; A61F 2/82; A61F 2/89; A61F 2/852; A61F 2/856; A61F 2/86; A61F 2/01; A61F 2/0103; A61F 2/0105; A61F 2/0108; A61F 2002/016; A61F 2/915; A61F 2002/9155; A61F 2002/91558; A61F 2002/91566; A61F 2002/91575; A61F 2002/91583
See application file for complete search history.

(56) References Cited

U.S. PATENT DOCUMENTS

| | | | |
|---|---|---|---|
| 5,906,606 A | 5/1999 | Chee et al. | |
| 6,004,310 A | 12/1999 | Bardsley et al. | |
| 6,022,374 A * | 2/2000 | Imran | A61F 2/91 623/1.34 |
| 6,293,966 B1 | 9/2001 | Frantzen | |
| 6,315,757 B1 | 11/2001 | Chee et al. | |
| 6,334,871 B1 * | 1/2002 | Dor | A61F 2/915 623/1.34 |
| 6,391,037 B1 | 5/2002 | Greenhalgh | |
| 6,503,271 B2 | 1/2003 | Duerig et al. | |
| 6,620,192 B1 | 9/2003 | Jalisi | |
| 6,702,782 B2 | 3/2004 | Miller et al. | |
| 6,855,161 B2 | 2/2005 | Boylan et al. | |

(Continued)

FOREIGN PATENT DOCUMENTS

| | | |
|---|---|---|
| DE | 10235868 | 2/2004 |
| EP | 2438891 | 4/2012 |

OTHER PUBLICATIONS

Co-Pending, co-owned U.S. Appl. No. 16/441,389, filed Jun. 14, 2019.

*Primary Examiner* — Wade Miles
(74) *Attorney, Agent, or Firm* — Cohen & Hildebrand, PLLC

(57) ABSTRACT

An expandable mechanical device for use during a thrombectomy medical procedure having enhanced visibility during imaging. Furthermore, the configuration of the eyelet and/or strut optimizes retention of the marker in the eyelet during the medical procedure without increasing overall profile of strut.

8 Claims, 13 Drawing Sheets

(56) References Cited

U.S. PATENT DOCUMENTS

| | | |
|---|---|---|
| 6,863,685 B2 | 3/2005 | Davila et al. |
| 6,929,635 B2 | 8/2005 | Shelso |
| 6,955,685 B2 | 10/2005 | Escamilla et al. |
| 7,063,707 B2 | 6/2006 | Bose et al. |
| 7,335,227 B2 | 2/2008 | Jalisi |
| 7,708,771 B2 | 5/2010 | Chuter et al. |
| 7,766,049 B2 | 8/2010 | Miller et al. |
| 7,810,223 B2 | 10/2010 | Hemerick et al. |
| 8,021,418 B2 | 9/2011 | Gerberding et al. |
| 8,313,503 B2 | 11/2012 | Cully et al. |
| 8,337,520 B2 | 12/2012 | Cully et al. |
| 8,500,786 B2 | 8/2013 | Simpson et al. |
| 8,500,787 B2 | 8/2013 | Simpson et al. |
| 8,545,548 B2 | 10/2013 | Lorenzo |
| 8,623,071 B2 | 1/2014 | Lundkvist et al. |
| 8,852,205 B2 | 10/2014 | Brady et al. |
| 8,926,560 B2 | 1/2015 | Dinh et al. |
| 8,974,517 B2 | 3/2015 | Pelton et al. |
| 9,011,374 B2 | 4/2015 | Lentz et al. |
| 9,232,992 B2 | 1/2016 | Heidner |
| 9,232,997 B2 | 1/2016 | Sugimoto et al. |
| 9,445,829 B2 | 9/2016 | Brady et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,693,885 B2 | 7/2017 | Lorenzo |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2004/0088039 A1 | 5/2004 | Lee et al. |
| 2004/0143317 A1 | 7/2004 | Stinson et al. |
| 2004/0167619 A1* | 8/2004 | Case ................... A61F 2/2418 623/1.34 |
| 2006/0064151 A1 | 3/2006 | Guterman |
| 2006/0212068 A1 | 9/2006 | Boylan et al. |
| 2007/0266542 A1 | 11/2007 | Melsheimer |
| 2007/0276476 A1 | 11/2007 | Llanos et al. |
| 2008/0281350 A1 | 11/2008 | Sepetka |
| 2009/0005853 A1 | 1/2009 | Osman |
| 2010/0324649 A1 | 12/2010 | Mattsson |
| 2011/0245806 A1 | 10/2011 | Patterson |
| 2012/0089219 A1 | 4/2012 | Fircho et al. |
| 2012/0283768 A1 | 11/2012 | Cox et al. |
| 2013/0319603 A1 | 12/2013 | Wu |
| 2014/0135812 A1 | 5/2014 | Divino et al. |
| 2014/0200607 A1 | 7/2014 | Sepetka et al. |
| 2015/0174363 A1 | 6/2015 | Sutermeister et al. |
| 2015/0305826 A1 | 10/2015 | Loganathan et al. |
| 2016/0001040 A1 | 1/2016 | Yamaguchi et al. |
| 2016/0008152 A1 | 1/2016 | Green |
| 2016/0015402 A1 | 1/2016 | Brady et al. |
| 2016/0022292 A1 | 1/2016 | Stigall et al. |
| 2016/0058971 A1 | 3/2016 | Leeflang et al. |
| 2016/0354584 A1 | 12/2016 | Hanson et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056616 A1 | 3/2017 | Leeflang et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172769 A1 | 6/2017 | Ta et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231646 A1 | 8/2017 | Epstein et al. |
| 2017/0231749 A1 | 8/2017 | Perkins et al. |
| 2017/0252064 A1 | 9/2017 | Staunton |
| 2017/0259034 A1 | 9/2017 | Leeflang et al. |
| 2017/0265983 A1 | 9/2017 | Lam et al. |

(56) References Cited

U.S. PATENT DOCUMENTS

| | | |
|---|---|---|
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

\* cited by examiner

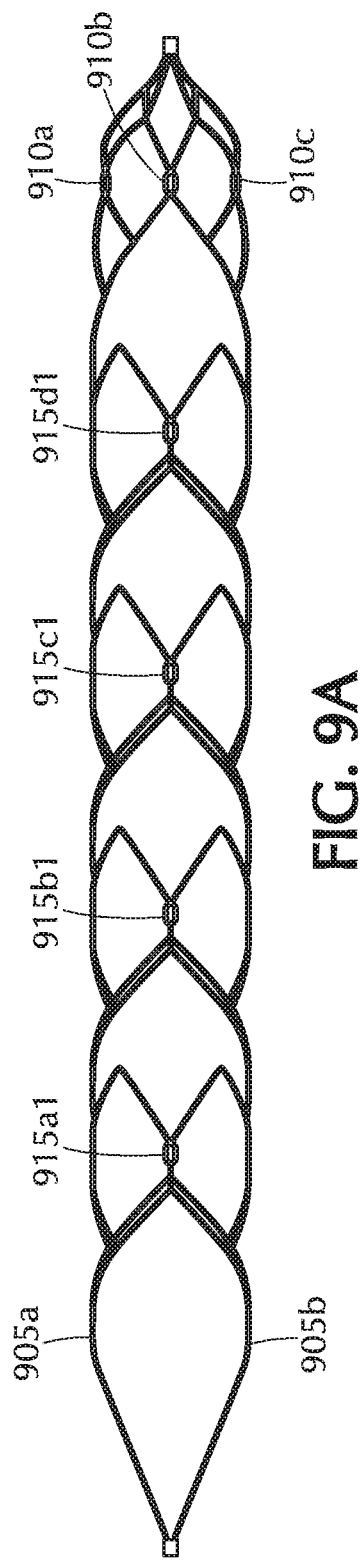
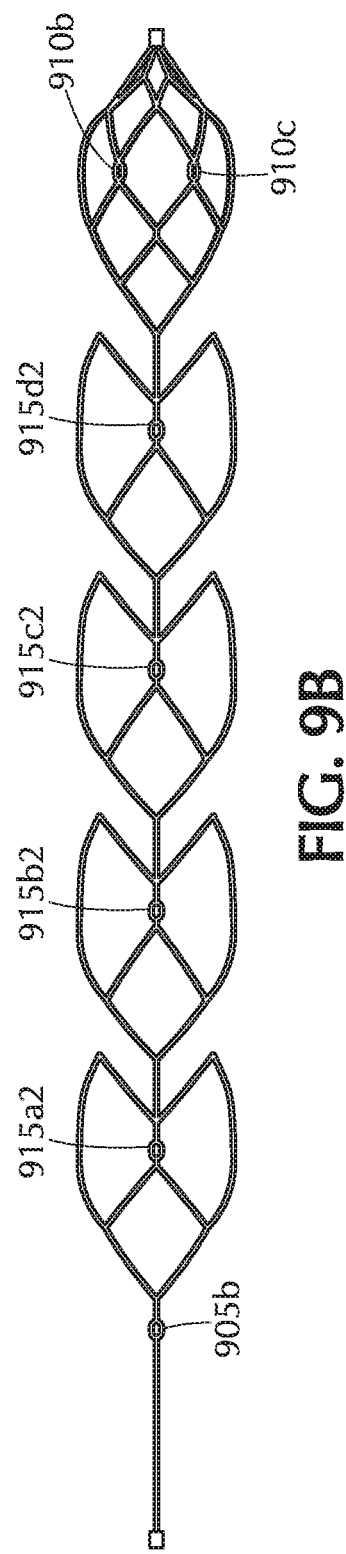
FIG. 9A
FIG. 9B

VISIBILITY OF MECHANICAL THROMBECTOMY DEVICE DURING DIAGNOSTIC IMAGING

BACKGROUND OF THE INVENTION

Field of the Invention

The present invention relates to an endovascular medical system. In particular, the present invention is directed to an improved mechanical thrombectomy device with enhanced visibility during diagnostic imaging.

Description of Related Art

Acute ischemic stroke is caused by a thrombotic or embolic occlusion (e.g., blockage) in a cerebral artery of the brain. The occlusion is typically caused by a blood clot liberated from another part of the body which travels in an anterograde direction (in the direction of normal blood flow) through the vessel and eventually become lodged in the cerebral artery of the brain. Clots are subject to a pulsatile pressure gradient (i.e., systemic blood pressure acting on the proximal thrombus face minus the pressure from retrograde collateral blood flow at the distal thrombus face) which may compact and further wedge in place the clot within the vessel over time. In addition, some degree of biological adhesion may occur between the clot and the interior wall of the vessel.

A procedure known as a thrombectomy may be used to remove the thrombus, occlusion, blockage or clot lodged in the vessel using a mechanical device. Thrombectomy treatment or procedure is typically performed on patients within a relative short period of time following a stroke (e.g., less than an approximately 48-hour period after the occurrence of a stroke) and is best suited for large vessel occlusions typically with a diameter greater than approximately 1.0 mm. Imaging, for example, angiography, MRI, CT or CT angiography (CTA), is typically used to determine if thrombectomy treatment is suitable for that particular patient.

During the thrombectomy procedure or treatment a physician or interventionalist endovascularly introduces a guidewire through the vasculature, typically in an artery located in the groin or arm, or by direct access through the carotid artery. The guidewire is advanced through the vasculature to the target location of the clot, blockage or occlusion. Once the guidewire is properly positioned, a microcatheter with an outer diameter typically less than approximately 1.0 mm, tracks over the guidewire passing through a lumen defined axially through the microcatheter. The guidewire and microcatheter are used to cross the clot or occlusion using standard intervention techniques. While in a compressed state, a stent or mechanical thrombectomy device may be guided through the lumen of the microcatheter to the target site. Upon deployment from the microcatheter the stent or mechanical thrombectomy device automatically expands to its original enlarged state. Stents or mechanical thrombectomy devices are typically made of a biocompatible material such as stainless steel, nickel-titanium or tantalum.

Thrombectomy procedures are conducted in a cardiac catheterization laboratory of a medical facility assisted by diagnostic imaging, typically fluoroscopy (i.e., continuous x-ray imaging). During thrombectomy procedures diagnostic imaging assists the interventionalist or physician to deploy the thrombectomy device in the optimum position in the occlusion. It may also help to visualize the shape of the vessel, the location of the thrombus on the mechanical thrombectomy device and if the thrombus retracts (withdrawals proximally through the vessel) at substantially the same speed as the mechanical thrombectomy device. Diagnostic imaging may also be used to determine if there is an underlying stenosis in the vessel.

Conventional mechanical thrombectomy devices are typically constructed of Nitinol (55 w. % Nickle, balance Titanium) or other super-elastic or shape memory alloy that is deformable/compressible, yet automatically (i.e., without the need for application of any external physical force) returns ("remembers") to its pre-deformed original shape when deployed or heated. FIG. 1 is a radial cross-sectional view of a conventional wire 100 made only of a single material, e.g., Nitinol. Laser cuts or other conventional techniques are typically used to create a desired pattern, e.g., an expandable mesh like skeleton or cage. In this example, five laser cuts are made radially inward from the outer diameter (OD) to the center (C) of the Nitinol wire to form five struts or pie shape wedges 105. Of course, any number of cuts may be made to form a desired number of two or more struts or pie shape wedges.

The shape memory alloy is subsequently set in a secondary shape by positioning on a mandrel and heating. The shape memory alloy advantageously provides a sturdy skeleton or frame while its elasticity properties allows it to recover its original shape after being deformed to be receivable within the lumen of the microcatheter. Because of the ability to set the shape of the mechanical device through mechanical constraint and heat treatment, the nitinol piece may be produced in a geometry that collapses (wraps down) to a smaller or reduced radius after being forced into the lumen of a catheter. Once the mechanical device is unsheathed from the distal end of the catheter it automatically recovers or reverts to its larger radius geometry. Despite these beneficial characteristics, one significant drawback associated with using a shape memory alloy for manufacture of the mechanical thrombectomy device is its relatively poor visibility under fluoroscopic imaging, that is, its relatively low radiopacity. To circumvent this shortcoming, conventional mechanical thrombectomy devices often are designed to incorporate additional radiopaque components (e.g., markers) such as platinum coils or gold rivets in order to improve visibility during diagnostic imaging.

The present invention is directed to an improved mechanical thrombectomy device having enhanced visibility during diagnostic imaging (e.g., fluoroscopy).

SUMMARY OF THE INVENTION

An aspect of the present invention is directed to a thrombectomy device with improved visibility during diagnostic imaging.

Another aspect of the present invention relates to an expandable mechanical device for use during a vascular medical procedure, wherein the device includes a strut having an eyelet defined therein having a geometric shape that includes at least one indent or outdent. Secured within the eyelet of the strut is a marker rivet. The geometric shape of the eyelet may include one or more indent or outdent. In addition, the indents or outdents in the eyelet may be mirror symmetrical images of one another along a longitudinal axis and/or a lateral axis. In a particular configuration, the geometric shape of the eyelet may be one of a butterfly bandage shape, a rocket shape, or a bow tie shape.

Yet another aspect of the present invention is directed to an expandable mechanical device for use during a vascular medical procedure including a strut having an outer surface and an outer diameter radial profile, wherein a recess is defined in the outer surface of the strut and extends radially inward. The device also including a U shape marker rivet received and secured within the recess of the strut. After assembly, an overall radial profile of an assembly of the strut and the U shape marker rivet is equal or less than the outer diameter radial profile of the strut alone, preferably flush with one another. In such configuration the recess may be an annular groove or an angled recess having a wedge shape radial cross-sectional profile.

Still another aspect of the present invention relates to an expandable mechanical device for use during a vascular medical procedure, the device including a plurality of struts each having an eyelet defined therein. Adjacent of the eyelets are positioned along a longitudinal axis of the mechanical device being radially offset relative to one another.

While still further another aspect of the present invention is directed to an expandable mechanical device for use during a vascular medical procedure, the device including a strut having an eyelet defined therein, the eyelet having tapered side walls forming one or more stepped layers. A marker rivet is secured within the eyelet of the strut.

Yet another aspect of the present invention relates to an expandable mechanical device for use during a vascular medical procedure, the device including a strut with an eyelet having walls defined therein. Along at least one of an outermost top edge or an innermost bottom edge of the walls of the strut having a chamfer cut.

In accordance with the present invention still another aspect is directed to an expandable mechanical device for use during a vascular medical procedure, the device including a strut having an eyelet defined therein and a strut profile, wherein the eyelet has an S shape. A complementary S shape marker rivet is secured within the S shape eyelet of the strut.

Another aspect of the present invention relates to an expandable mechanical device for use during a vascular medical procedure, the device including a single strut defined between two adjacent crowns of the expandable medical device. The single strut has a set of plural eyelets defined therein; and within each of the plural eyelets in the set a marker rivet is secured. In one aspect of the invention the plural eyelets in the set overlap one another in series, while in another aspect of the invention the plural eyelets in the set are arranged in linear series one after the other without overlap.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 9A is a plan view of an exemplary outer cage having two proximal radiopaque markers, three distal radiopaque markers, and four intermediate radiopaque marker sets (each set having four intermediate markers) disposed therebetween;

FIG. 9B is a side view of the exemplary outer cage of FIG. 9A;

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot" or "blockage" are used interchangeably.

Figure 2:
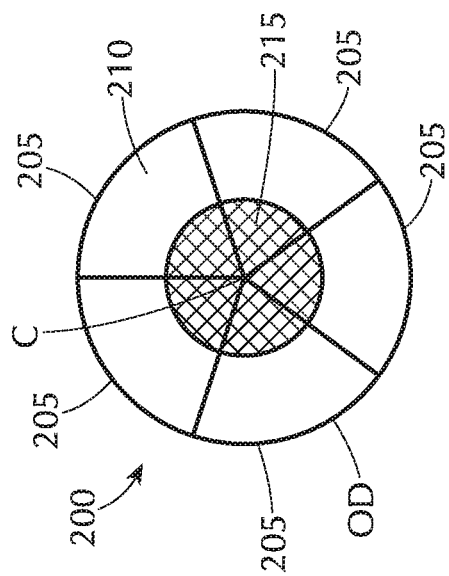
FIG. 2 is a radial cross-sectional view of a Prior Art drawn filed tube (DFT) composite wire made of two different materials in accordance with the present invention; an inner core formed of a radiopaque material is surrounded by an outer metal layer; the composite wire has been laser cut radially inward from its outer perimeter to its center to form five equally sized pie shape wedges or segments.

Referring to FIG. 2, a radial cross-sectional view of an exemplary Prior Art drawn filled tube (DFT) composite wire 200 to produce a mechanical thrombectomy device is illustrated. The wire in FIG. 2 has an inner core 215 made of a first biocompatible material surrounded by an outer layer 210 of a second biocompatible material that differs from the first material. The first material forming the inner core 215 is made of a radiopaque material, that is, a material that is opaque to one or another form of radiation, such as X-rays, in order to be visible during imaging. Preferably, the first material has a relatively high radiopacity, typically materials with a high atomic number (e.g., atomic numbers in the 70's) such as platinum, gold, tantalum or tungsten. The second material comprising the outer layer 210 is a shape memory alloy such as Nitinol (Nickle-Titanium metal alloy). The formed drawn filled composite tube made from two different materials may then be cut radially inward, preferably using an ultra-high frequency laser, through the outer layer and inner core to its center (not through the wire completely). What is formed are a plurality of wedge or pie shape struts. In the exemplary embodiment in FIG. 2, five wedge or pie shape struts 205 are defined. Of course, the drawn filled tube wire may be laser cut, as desired, to define any number of one or more wedge or pie shape struts. Each strut may be expanded on a mandrel and heat-set, as per standard Nitinol device production.

Figure 3:
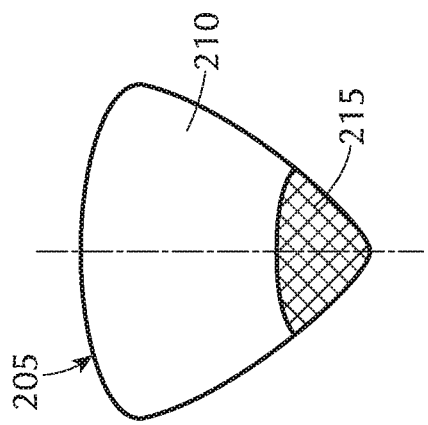
FIG. 3 is one of the expanded struts of FIG. 2.
Figure 1:
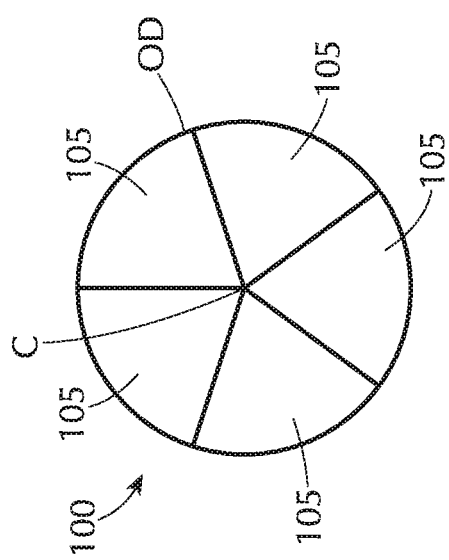
FIG. 1 is a radial cross-sectional view of a Prior Art conventional wire made of a single material (Nitinol) that has been laser cut radially inward from its outer perimeter to its center to form five pie shape wedges or segments.

From the single expanded strut 205 shown post polishing depicted in FIG. 3 it is clearly visible that each strut (all struts in the drawn filled tube wire) produced in accordance with the present invention comprises a section or portion of the inner core 215 made of a radiopaque material, e.g., platinum in the exemplary embodiment shown. Since every strut comprises some portion thereof made from a radiopaque material the complete or entire mechanical thrombectomy device is visible during diagnostic imaging.

Figure 4A:
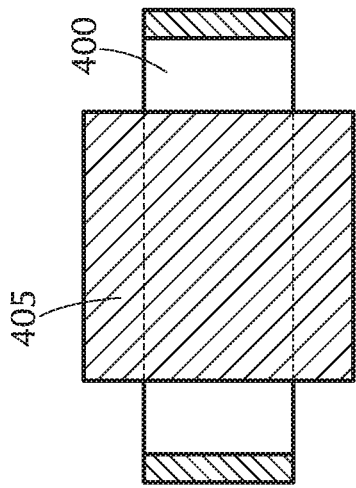
FIG. 4A is a plan view of a single eyelet and associated radiopaque marker rivet of a Prior Art mechanical thrombectomy device prior to crimping of the rivet (i.e., pre-riveted)
Figure 4B:
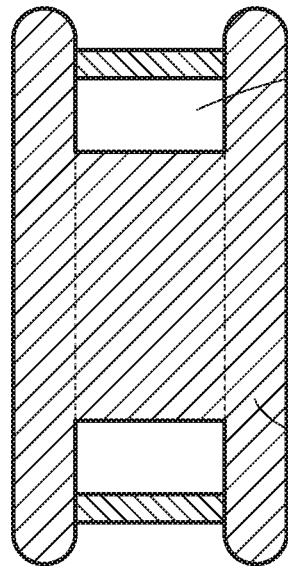
FIG. 4B is a cross-sectional view of the single eyelet and associated radiopaque marker rivet of the Prior Art mechanical thrombectomy device of FIG. 4A along lines 4B-4B.
Figure 4C:
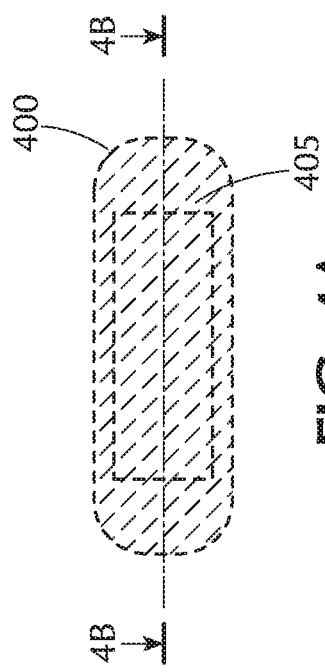
FIG. 4C is a plan view of the single eyelet and associated radiopaque marker rivet of the Prior Art mechanical thrombectomy device in FIG. 4A after the rivet has been crimped in position (i.e., post-riveted)
Figure 4D:
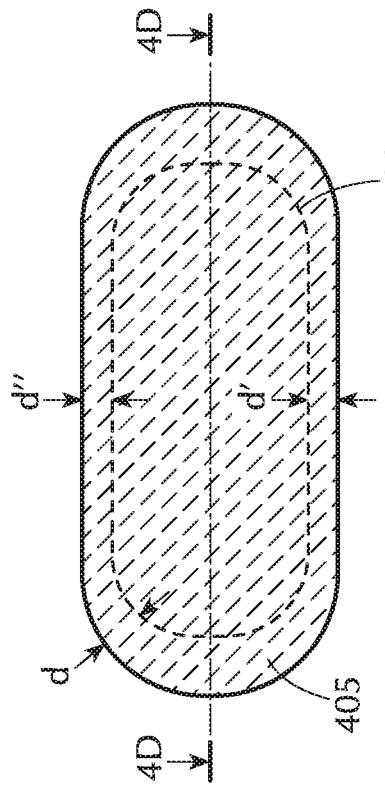
FIG. 4D is a cross-sectional view of the single eyelet and associated radiopaque marker rivet of the Prior Art mechanical thrombectomy device of FIG. 4C along lines 4D-4D.

As previously mentioned above, the radiopacity and hence visibility during diagnostic imaging of the mechanical thrombectomy device may be improved by attaching or securing to the struts of the stent one or more markers made of a material having a greater radiopacity (e.g., gold, platinum or tantalum) than that of the strut. FIGS. 4A & 4B, show a plan view of a single eyelet or opening 400 of a strut of a prior art mechanical thrombectomy device (e.g., stent) and an associated or corresponding single rivet 405 (made of a radiopaque material) before the rivet is crimped within the eyelet (i.e., pre-rivet). The cross-sectional view along lines 4B-4B of the eyelet and corresponding rivet is illustrated in FIG. 4B. This conventional shape eyelet is oval or ovoid in shape, and the associated marker rivet also has an oval, ovoid or rectangular cross-sectional profile (FIG. 4A). After crimping (i.e., post riveting), as represented in the plan view of FIG. 4C, there exists a contact or overlap area between the crimped marker rivet and the eyelet of a distance (d, d', d"). FIG. 4D is a cross-sectional view through the eyelet and rivet (post riveting) along lines 4D-4D of FIG. 4C.

Figure 5C:
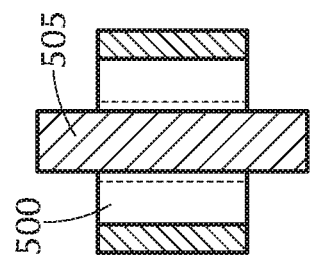
FIG. 5C is a cross-sectional view of the single eyelet and associated radiopaque marker rivet of the present inventive mechanical thrombectomy device of FIG. 5A along lines 5C-5C.
Figure 5B:
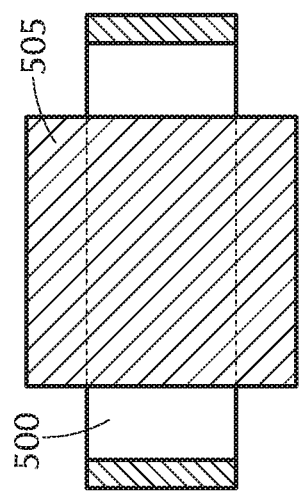
FIG. 5B is a cross-sectional view of the single eyelet and associated radiopaque marker rivet of the present inventive mechanical thrombectomy device of FIG. 5A along lines 5B-5B.
Figure 5A:
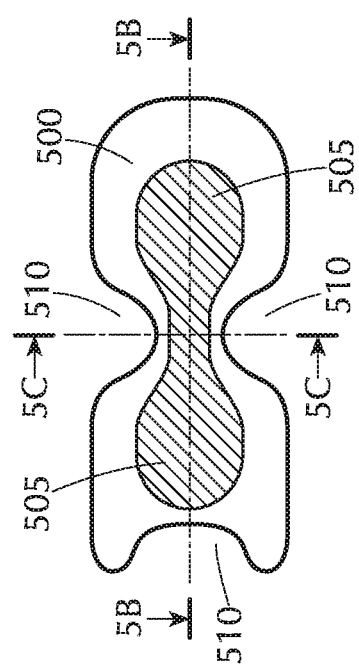
FIG. 5A is a plan view of a single eyelet and associated radiopaque marker rivet of a mechanical thrombectomy device in accordance with the present invention prior to crimping of the rivet (i.e., pre-riveted)
Figure 5F:
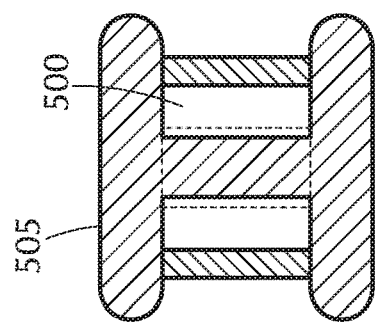
FIG. 5F is a cross-sectional view of the single eyelet and associated radiopaque marker rivet of the present inventive mechanical thrombectomy device of FIG. 5D along lines 5F-5F.
Figure 5E:
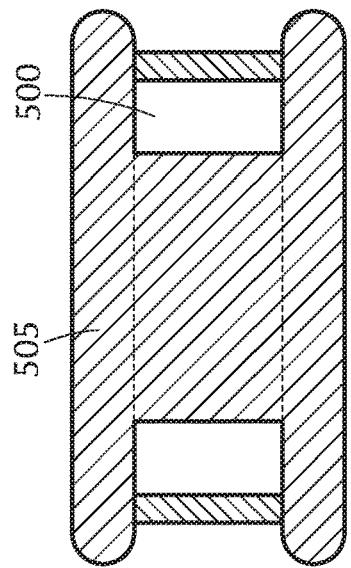
FIG. 5E is a cross sectional view of is a cross-sectional view of the single eyelet and associated radiopaque marker rivet of the present inventive mechanical thrombectomy device of FIG. 5D along lines 5E-5E.
Figure 5D:
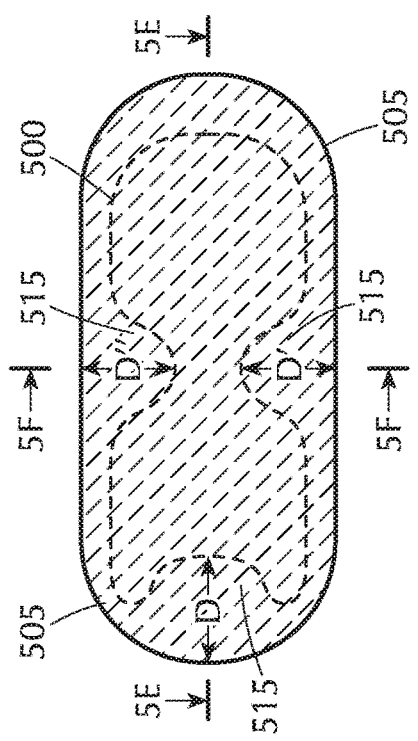
FIG. 5D is a cross-sectional view of the single eyelet and associated radiopaque marker rivet of the present inventive mechanical thrombectomy device of FIG. 5A after the rivet has been crimped in position (i.e., post-riveted)

To prevent dislodgement of the riveted marker from within the opening or eyelet of the struts of the stent, the present invention increases the contact area and overlap area, hence increasing the retention force of the rivet in the eyelet of the strut. Rather than the conventional oval cross-sectional profile of the eyelet (having no indents/recesses and/or outdents/protrusions) of prior art stents (FIGS. 4A-4D), the cross-sectional profile of the present inventive eyelet design depicted in FIGS. 5A-5F has one or more indents/recesses and/or outdents/protrusions in its cross-sectional profile. Preferably, the cross-sectional profile of the present inventive eyelet design has a plurality of indents/recesses and/or outdents/protrusions. In the exemplary plan view illustration in FIG. 5A, the cross-sectional profile of the eyelet resembles that of a butterfly shape bandage, a rocket shape, or a bow tie. This preferred geometric shape configuration of the eyelet is preferably tapered towards the middle from each of its respective sides, that is, opposing sides are drawn inward towards one another like a symmetric mirror image along line 5B-5B. Each indentation or recess 510 of the eyelet 500 in accordance with the present invention provides an increased or greater overlap area or surface (D, D', D") relative to that in the rectangular or oval eyelet conventional configuration (d, d', d")(FIG. 4C), wherein the overlap area or surface represents a region of the riveted marker extending radially outward from the outer profile of the eyelet, after crimping (i.e., post-riveting). The contact area between the side wall of the rivet and the side wall of the eyelet is also increased due to the increased contact surface. This increase in overlap area and contact surface improves retention of the riveted marker 505 within the corresponding eyelet 500. The number, location and positioning of the indentations or recesses 510 of the eyelet in accordance with the present invention, may be selected as desired, to impart enhance retention force preferably targeted to those areas prone to maximum bending, flexing and/or deformation during use.

Figure 6:
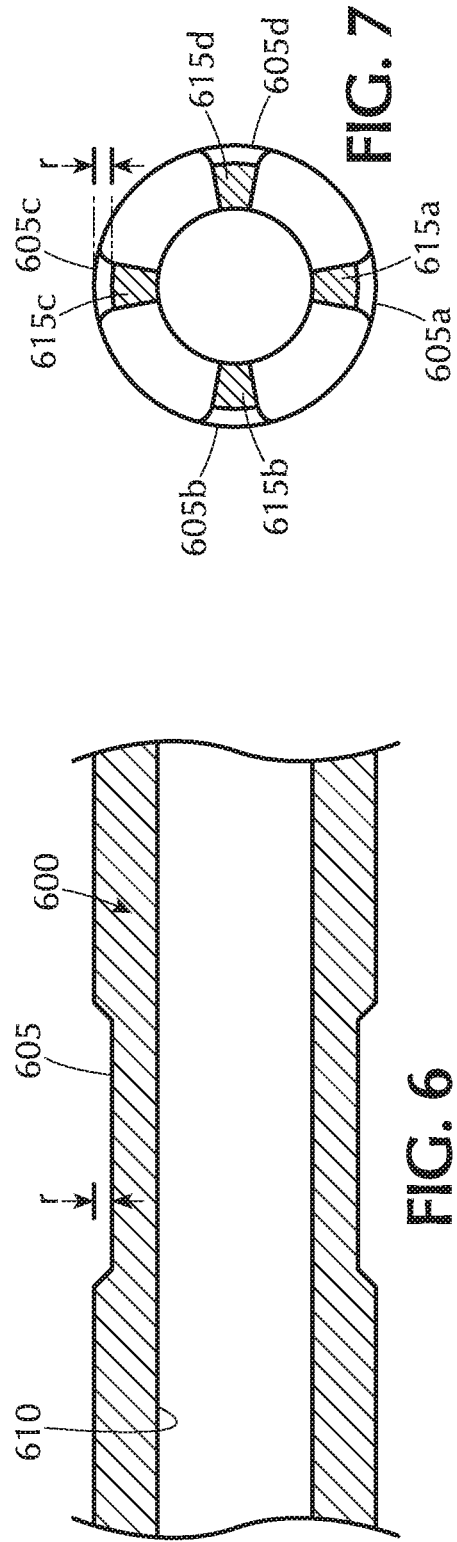
FIG. 6 is a longitudinal cross-sectional view of a portion of a raw shape memory alloy tubing in accordance with the present invention with an annular shape recess, channel or groove defined radially inward in a portion of its outer surface.

As an alternative to riveting radiopaque markers in the eyelets defined in the struts of the stent, the radiopacity of the mechanical thrombectomy device may be improved by crimping markers made of a radiopaque material (e.g., gold or platinum) directly to portions or segments of the strut itself. Such approach unfortunately results in an unwanted increase in the overall profile, i.e., an increase in the outer diameter (OD) and/or a decrease in the inner diameter (ID) of the crimped assembled device. With any increase in overall profile of the marker, its leading edge may disadvantageously act as a snag point during loading or re-sheathing. To overcome these problems, the outer surface or profile of the super memory alloy tubing 600 (e.g., Nitinol tubing), in accordance with the present invention, is processed to accommodate the swaging or welding thereto of the radiopaque markers without increasing the overall profile of the assembled components. Specifically, prior to laser cutting of the strut pattern, one or more annular recesses, channels or grooves 605 are defined radially inward by removing only a portion from the outer surface of the super memory alloy raw tubing 600, as illustrated in FIG. 6. Note that the annular recess, channel or groove does not penetrate the inner lumen 610. One or more annular recesses, channels or grooves 605 may be ground, laser machined or any other conventional technique for removal of only a portion of the outer surface of the super memory alloy tubing material 610. A single annular recess, channel or groove 605 is illustrated in the partial longitudinal view in FIG. 6 of the raw super memory alloy tube 600 (prior to being laser cut into a desired pattern and heated).

However, as previously noted, any number of one or more annular recesses, channels or grooves 605 may be defined in the outer surface of the tubing. The annular recess, channel or groove 605 is located where the desired radiopaque marker is to be positioned. Annular recess, channel or groove 605 has a radially inward depth "r" as measured from the outermost perimeter of the tubing to the opposing bottom surface of the annular recess, channel or groove that typically varies from approximately 10% to approximately 50% of the wall thickness. The radially inward depth "r", preferably, approximately 25-50 μm, is sufficient to accommodate a U shape or C shape marker to be crimped therein without the U shape or C shape marker extending radially outward beyond the outer diameter of the strut. Rather, the U shape or C shape marker is preferably flush with the outer diameter of the strut.

Figure 7:
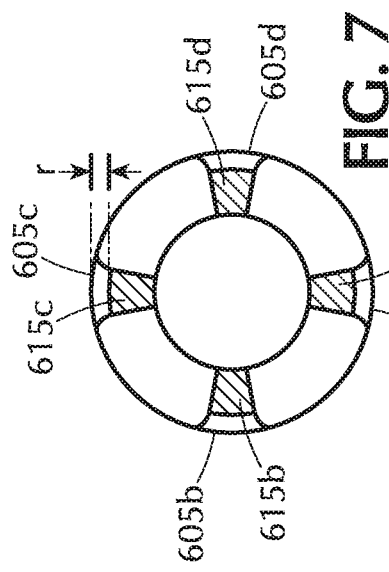
FIG. 7 is a radial cross-sectional view through an exemplary laser cut mechanical device having four struts each with a corresponding annular shape recess defined radially inward in its outer surface.

Once the material has been removed from the outer surface of the super memory alloy tubing to form the one or more annular recesses, channels or grooves the desired strut pattern may then be laser cut into the processed tubing so that following device expansion, the recesses may be aligned with the key strut locations of the device. In the exemplary radial cross-sectional profile in FIG. 7 the superelastic shape memory alloy tubing has been laser cut into a desired pattern having four struts (615a, 615b, 615c, 615d) each strut with an associated annular recess, channel or groove (605a, 605b, 605c, 605d) defined radially inward by removing a portion of the outer surface of the associated strut. Any number of one or more struts each having an associated annular recess, channel or groove may be formed, as desired. A respective marker is swaged or welded into a corresponding recess defined in the strut.

Figure 8:
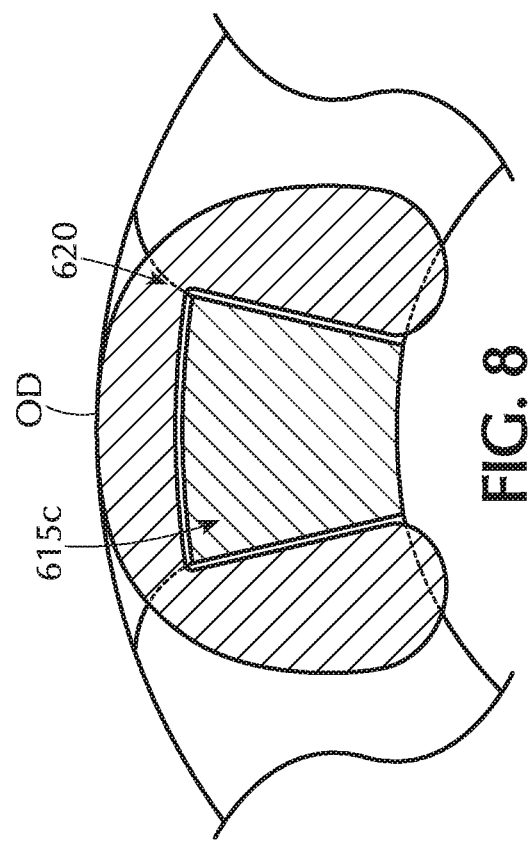
FIG. 8 is an enlarged partial radial cross-sectional view of a U shape or C shape marker swaged or welded within the annular shape recess of one of the struts in FIG. 7, illustrating that when the components are assembled together the marker does not extend radially outward beyond the outermost surface of the strut.

FIG. 8 is a cross-sectional view of a single U shape or C shape marker 620 crimped within the annular recess, channel or groove defined in the strut 615c. As a result of the annular recess, channel or groove defined in the outer surface of the strut, the outermost perimeter of the U shape or C shape marker 620 does not extend radially outward beyond that of the outermost diameter of the strut 615c. Hence there is no increase in overall profile of the assembled components (i.e., the outermost circumference of the U shape or C shape marker is either flush or radially inward of the outermost diameter (OD) of the strut thereby eliminating the possible risk of snagging.

Figure 14B:
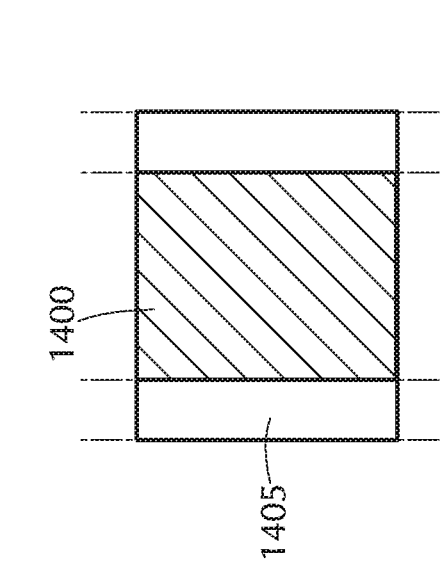
FIG. 14B is a top view of the angled recess of the strut in FIG. 14A.
Figure 14D:
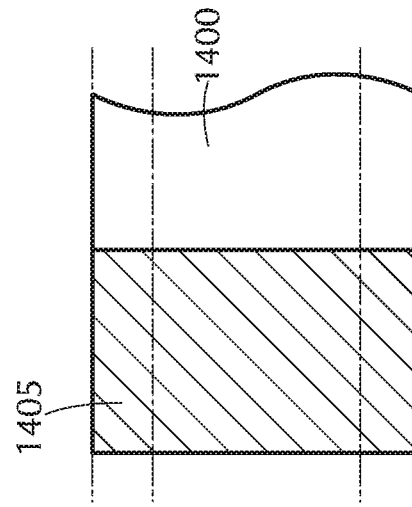
FIG. 14D is a side view of the angled recess of the strut in FIG. 14A.
Figure 14A:
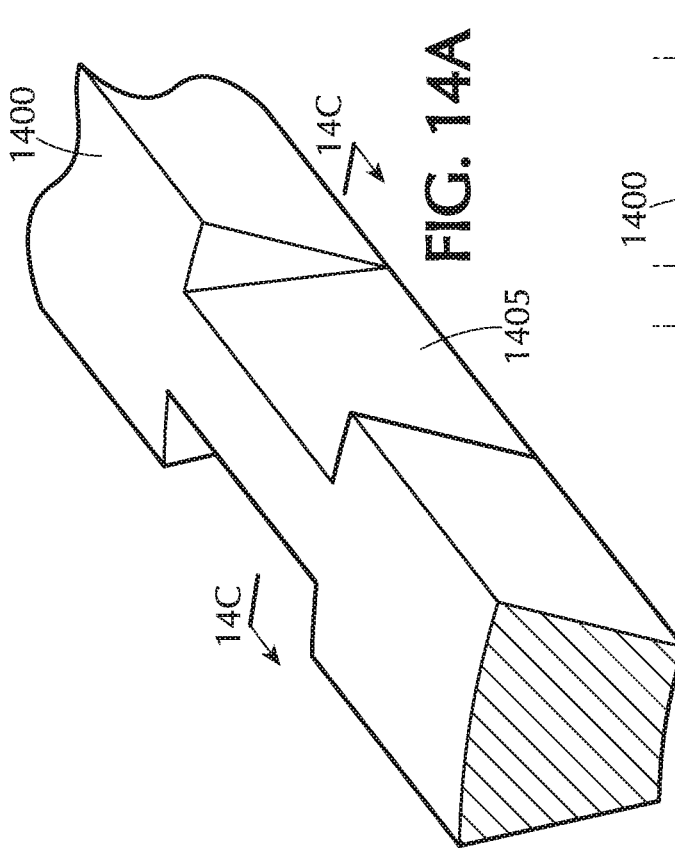
FIG. 14A is a perspective view of a strut with an angled recess defined in it outer perimeter.
Figure 14C:
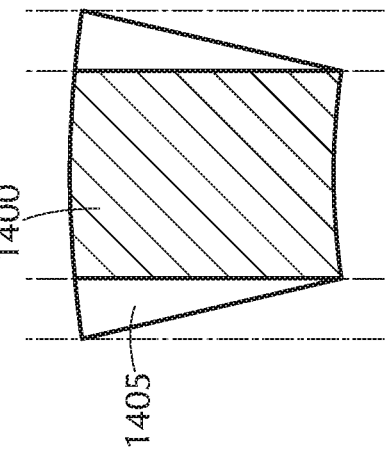
FIG. 14C is a cross-sectional view through the angled recess of the strut in FIG. 14A along lines 14C-14C.
Figure 14F:
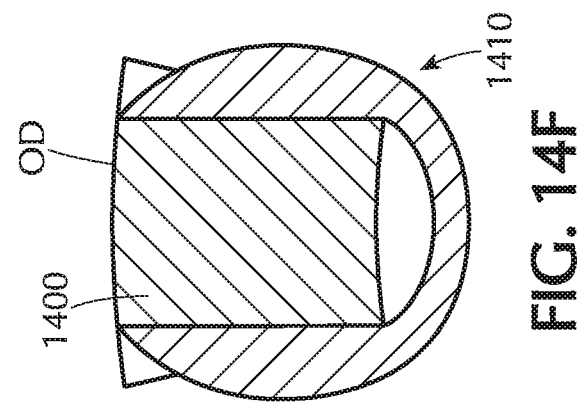
FIG. 14F is a cross-sectional view through the assembled strut of FIG. 14E along lines 14F-14F, illustrating that when assembled the C shape or U shape marker does not extend radially outward beyond the outer diameter of the strut.
Figure 14E:
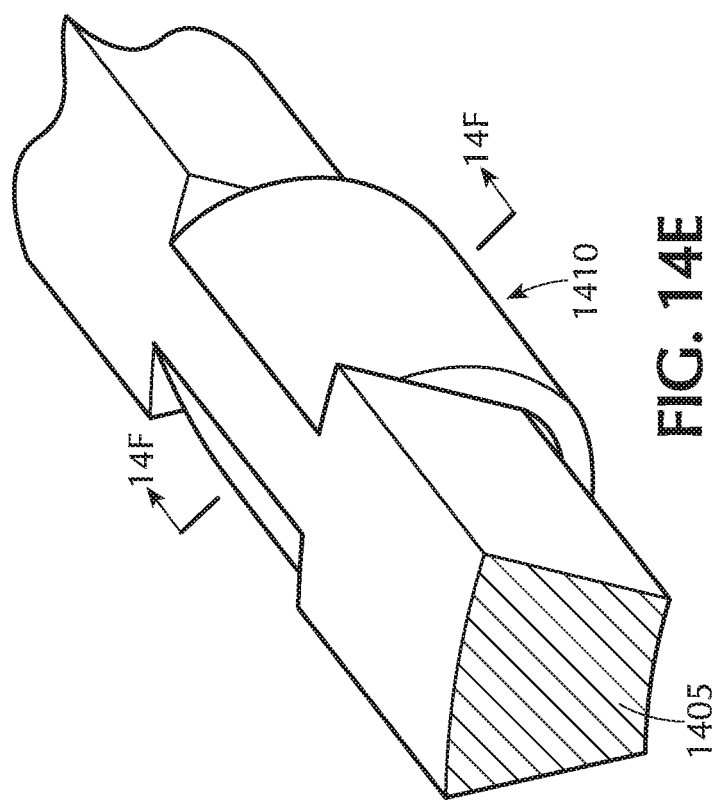
FIG. 14E is a perspective view of the assembled strut having an angled recess defined in it outer perimeter with a C shape or U shape marker secured therein.

An alternative configuration is depicted in FIGS. 14A-14F, wherein angled laser cuts are made into the strut resulting in removal of wedge-shape or pie-shape sections therefrom. FIG. 14A is a perspective view of an exemplary strut 1400 having pie-shape or wedge-shape recesses 1405 formed by several angled laser cuts. A top view and side view of the pie-shape or wedge-shape recess of the strut in FIG. 14A is illustrated in FIGS. 14B & 14D, respectively. While a partial cross-sectional view of the pie-shape or wedge shape recess of the strut in FIG. 14A along line 14C-14C is shown in FIG. 14C. Once one or more of the angled laser cuts have been made to the struts, thereafter a C shape or U shape marker 1410 is crimped, swaged, or welded in the respective recess, as illustrated in the perspective view of the assembled device in FIG. 14E. The angled laser cuts are made to the strut so that when assembled the marker does not extend radially outward beyond that of the outer diameter of the strut, as illustrated in FIG. 14F. Preferably, the C shape or U shape marker is flush with the outer diameter of the strut.

FIGS. 9A & 9B are plan and side views, respectively, of an exemplary outer cage 900 of a mechanical thrombectomy device. In this exemplary embodiment, cage 900 has two radiopaque markers 905a, 905b at its proximal end, three radiopaque markers 910a, 910b, 910c at its opposite distal end, and four intermediate marker sets (915a, 915b, 915c, 915d) therebetween, wherein each intermediate marker set comprises four intermediate markers. Specifically, the first intermediate marker set 915a comprises four intermediate marker segments ($915a_1$, $915a_2$, $915a_3$, $915a_4$), the second intermediate marker set 915b comprises four intermediate marker segments ($915b_1$, $915b_2$, $915b_3$, $915b_4$), the third intermediate marker set 915c comprises four intermediate marker segments ($915c_1$, $915c_2$, $915c_3$, $915c_4$), and the fourth intermediate marker set 915d comprises four intermediate marker segments ($915d_1$, $915d_2$, $915d_3$, $915d_4$). Any number of one or more radiopaque markers may be disposed along the struts of the cage at the proximal end, distal end or intermediate therebetween.

Figure 10:
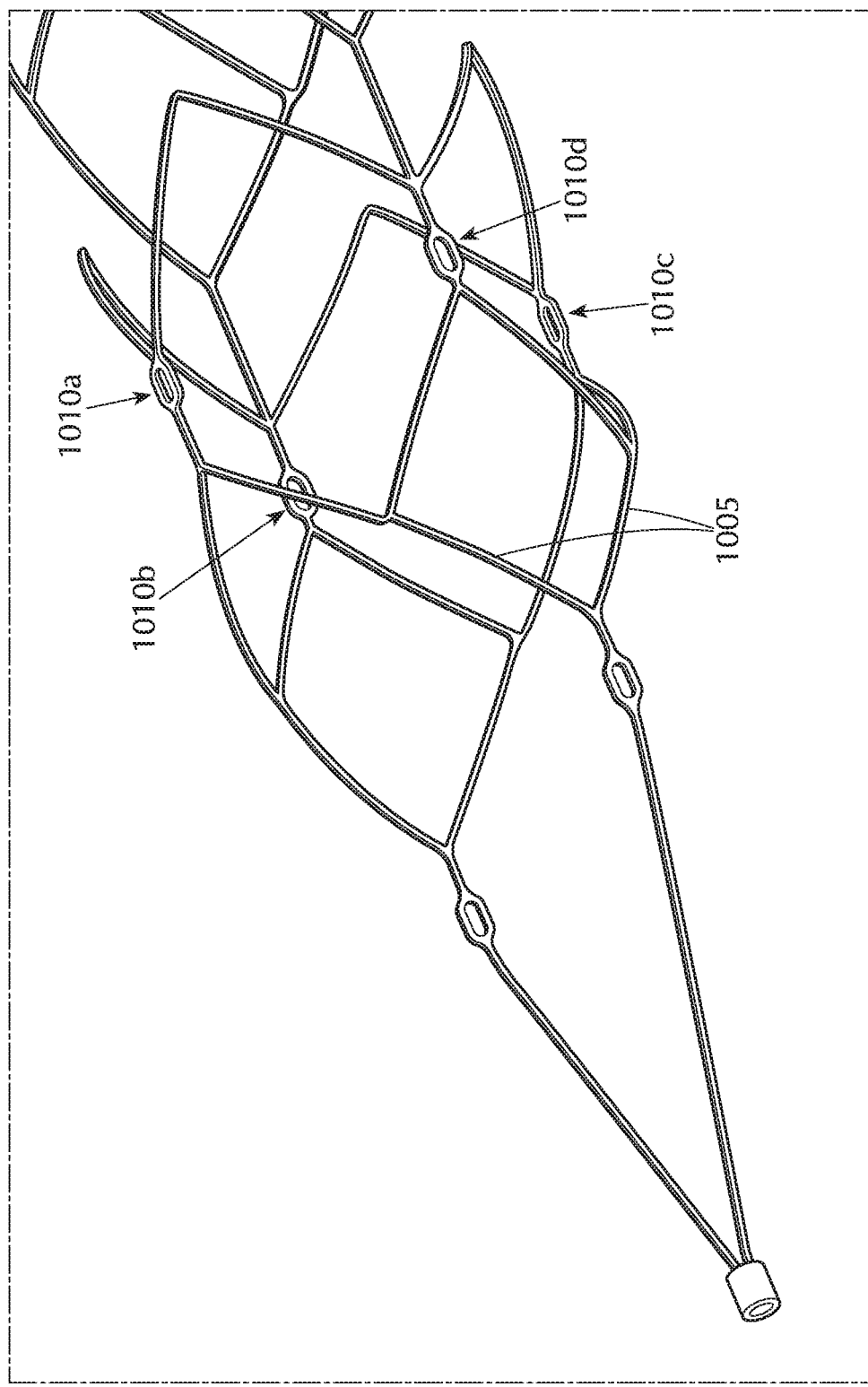
FIG. 10 shows an illustrative expanded cage comprising a plurality of struts or segments and exemplary rivet eyelet positions in a staggered (non-aligned) radial configuration to facilitate reduced profile efficient wrapping and compatibility with microcatheters having relatively small diameter lumen.

FIG. 10 is a perspective view of a portion of an illustrative cage 1000 in an expanded state depicting the struts or segments 1005 with four exemplary eyelet (1010a-1010d) positions for receiving therein an associated rivet made of a radiopaque marker material. Eyelets 1010a-1010d, and hence the radiopaque marker rivets to be received therein, are not aligned radially. Rather, eyelet 1010a and 1010c are aligned radially while 1010b and 1010d are staggered proximally or distally. Staggering of the eyelets and hence radiopaque marker rivets therein so that they are not aligned radially has the advantage of allowing the cage to wrap down (collapse) more efficiently to a smaller diameter for loading into the catheter.

Figure 11A:
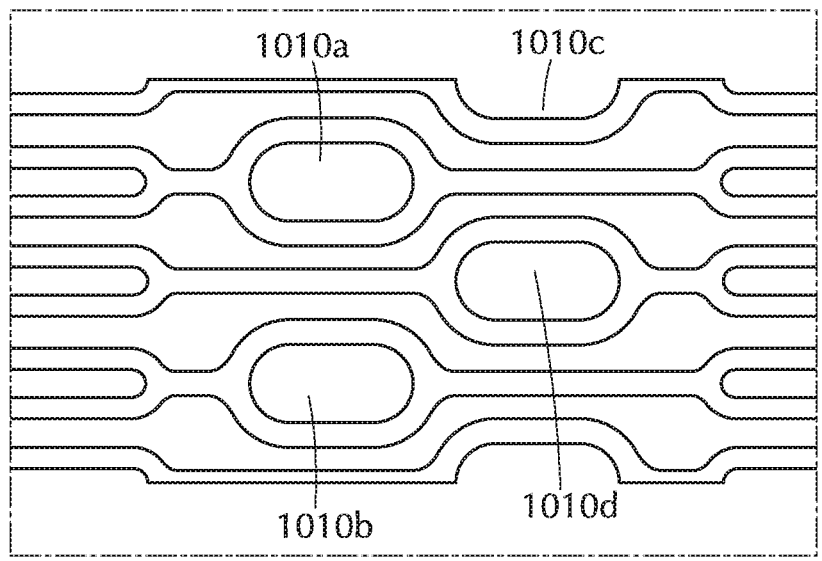
FIG. 11A is a portion of an unrolled laser cut pattern for an outer cage depicting the staggered or offset eyelets along the axial or longitudinal direction of the outer cage to facilitate reduced profile efficient wrapping and compatibility with relatively small diameter microcatheters.
Figure 11B:
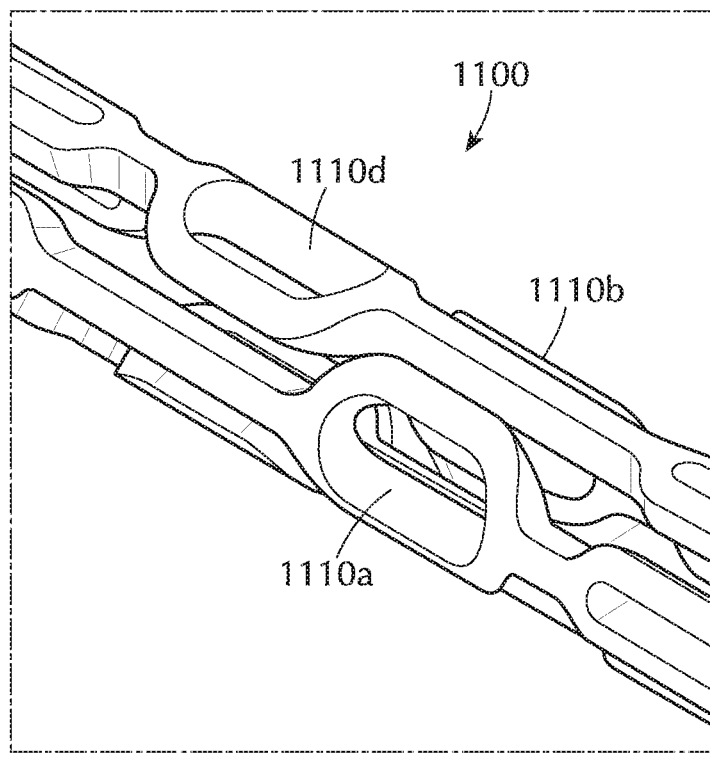
FIG. 11B is a perspective view of the portion of laser cut pattern of the outer cage of FIG. 11A after being rolled and while in a compressed state, prior to being expanded, illustrating the arrangement of the eyelets offset longitudinally along the axial direction of the outer cage.

FIGS. 11A & 11B, depict the laser cut pattern of the outer cage. Specifically, FIG. 11A depicts a portion of a flat, unrolled laser cut pattern for the outer cage 1100. As is clearly seen in this figure, adjacent eyelets 1110a-1110e are offset or staggered relative to one another in a longitudinal or axial direction along the outer cage 1100. Specifically, eyelet 1110a is offset relative to 1110d. Staggering or offsetting of the eyelets facilitates relatively low profile efficient wrapping of the outer cage in a compressed state making it more compatible to be received with the lumen defined in relatively small diameter microcatheters. A portion of the laser cut pattern for the outer cage 1100 while in a rolled configuration, prior to expansion, is depicted in the perspective view of FIG. 11B. Once again, the staggered or offset arrangement in a longitudinal or axial direction of the cage of adjacent eyelets (1110a-1110e) relative to one another is evident in FIG. 11B.

Figure 12A:
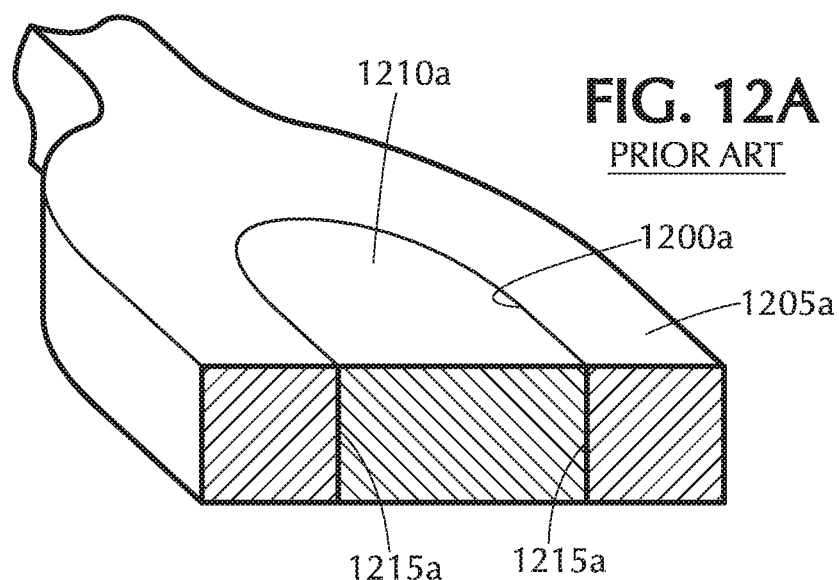
FIG. 12A is a cross-sectional view of a prior art assembled strut defining an eyelet and an associated marker rivet secured therein without any overhang of the maker rivet over the eyelet.
Figure 12B:
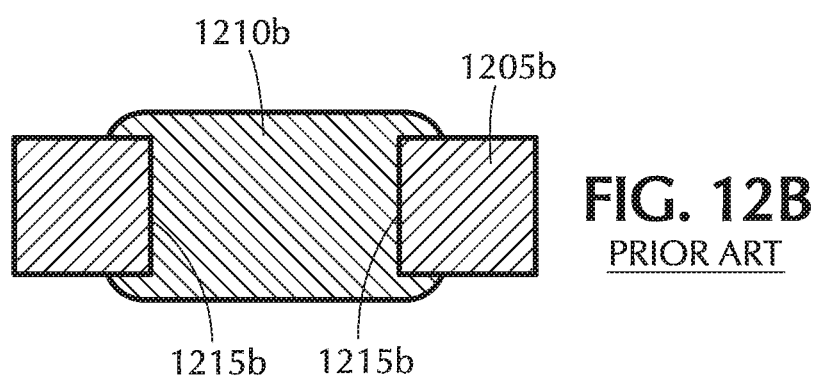
FIG. 12B is a cross-sectional view through a prior art assembled strut defining an eyelet and an associated marker rivet secured therein creating an overhang effect at both the outermost/top surface and the lowermost/bottom surface, thereby disadvantageously increasing the overall profile of the assembled components.
Figure 12C:
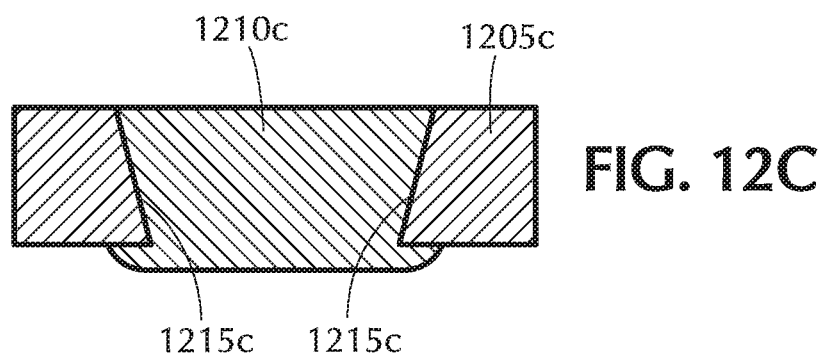
FIG. 12C is a cross-sectional view in accordance with the present invention of an assembled strut defining an eyelet with tapered or angled side walls produced by an offset laser cut and an associated marker rivet secured therein creating an increased overhang effect and improved retention.

Each marker rivet is secured in place within an associated eyelet defined in the strut to avoid dislodgement during the medical procedure. Retention of the marker in the eyelet is sufficient to resist forces acting to dislodge the rivet in the direction of the inside of the strut towards the outside and from the outside of the strut towards the inside. An overhang of the marker over that of the eyelet is a typical method used to improve securement of the components with the disadvantage of creating an increase in overall profile. FIG. 12A is a cross-sectional view of a prior art assembled rivet 1210a within an associated eyelet 1200a having side walls 1215a which are substantially parallel in this configuration, forming a rectangular or square wedge strut cross-section 1205a. In this design there is no overhang of the rivet over the eyelet of the strut, and minimal (if any) angle of the side wall, hence the marker is prone to dislodgement from the eyelet during the medical procedure. Also known in the prior art is to allow the marker rivet 1210b to overhang both at the top and bottom surface of the parallel side walls forming the eyelet 1200b, as illustrated in FIG. 12B. This design reduces the occurrence of dislodgement, at the sacrifice of an increased overall profile due to the overhang. A modified design in accordance with the present invention is depicted in FIG. 12C having an eyelet 1200c whose side walls 1215c are significantly angled or tapered (like that of a trapezoid), due to cutting with a laser which is offset from the centerline of the tubing, with a smallest distance separation between opposing side walls at its innermost/bottom surface and a largest distance separation between opposing side walls at its outermost/top surface. The rivet 12010c secured therein to the eyelet 1200c has an overhang only on the innermost/bottom surface (where such increased profile is of less concern), without any overhang at the outermost/top surface. The angled sidewall provides improved retention particularly against forces acting to push the maker towards the inside or center axis of the device while the overhang on the innermost surface provides improved retention particularly against forces acting to push the marker from the inside towards the outside of the device.

Figure 12D:
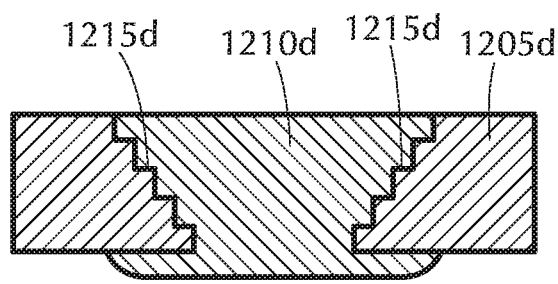
FIG. 12D is a cross-sectional view in accordance with the present invention of an assembled strut defining an eyelet with tapered or angled side walls having stepped or staggered layers and an associated marker rivet secured therein creating an increased overhang effect and improved retention.
Figure 12E:
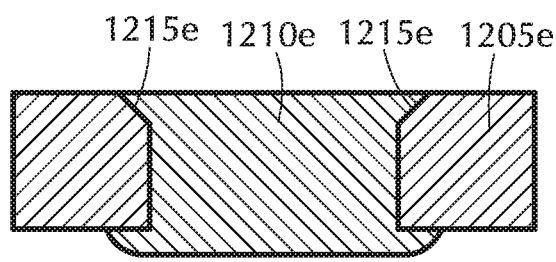
FIG. 12E is a cross-sectional view in accordance with the present invention of an assembled strut defining an eyelet having a single chamfer along its outermost/top surface and an associated marker rivet secured therein creating an overhang effect and improved retention.
Figure 12F:
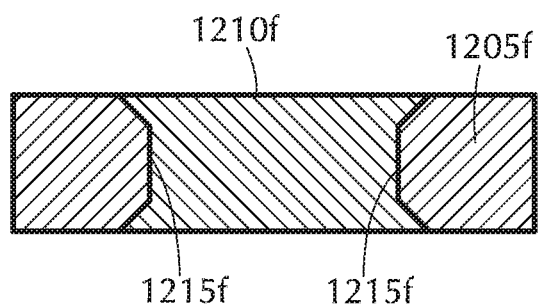
FIG. 12F is a cross-sectional view in accordance with the present invention of an assembled strut defining an eyelet having a double chamfer along both its outermost/top surface and opposite innermost/bottom surface and an associated maker rivet secured therein, improving retention without creating an overhang effect or increasing overall profile.

It is therefore desirable to develop a still further enhanced design for secure marker retention in an eyelet defined in a strut without the undesirable trade off of increase in overall profile that makes it difficult to wrap down the mechanical device during delivery through a microcatheter. A novel design in accordance with the present invention has the tapered or angled side walls 1215d of the eyelet 1200d further defined by a plurality of steps or staggered tapered layers defined in the strut 1205d, (FIG. 12D). Such steps or layers in the tapered or angled side walls 1215d are beneficial as they may be produced with a standard laser set up by cutting a series of rings with reducing diameters. This gives the same benefits as the design shown in FIG. 12C, but without requiring the laser to cut off center. In cross-sectional views FIGS. 12E & 12F, the walls (1215e, 1215f) of the strut cross-section have a single chamfer (only at its outermost/top surface) or a double chamfer (chamfered at both its outermost/top surface and innermost/bottom surface) defined in the strut, respectively. A chamfer is herein defined as an angled or sloping surface at an edge or corner of the side wall of the strut. On the one hand, the single chamfer configuration creates an overhang effect only along the inside where an increase in profile or volume is not as much concern, while no overhang profile exists on the outmost/top surface. While, on the other hand, the double chamfer design, provides enhanced retention without any increase whatsoever in profile (either along its outermost/top surface or innermost/bottom surface). An offset laser can be used to create the single or double chamfer configuration of FIG. 12E.

Mechanical thrombectomy procedures are typically performed under fluoroscopy and radiopaque markers on the mechanical thrombectomy device provide the interventionalist with a visual indication of the position and expansion/crimped state of a device during the medical procedure. By way of illustrative example, information provided by visual indicators of use to an interventionalist during the medical procedure may include: position of the device in the microcatheter on delivery; expansion of the device on deployment; changes in expansion of the device on retrieval.

Radiopaque markers arranged in clearly defined rings around the circumference at several locations along the mechanical device provide observable information to the physician or interventionalist during the medical procedure. Typically, during a procedure there are two fluoroscopic views used by the physician or interventionalist, namely, the anterior-posterior view (parallel with a patient's torso) and lateral view (parallel with patient side). Distinguishing the ring a particular identified marker belongs to is potentially beneficial and may be a challenge for the physician or interventionalist.

The present invention seeks to improve the visibility of the marker and geometrically differentiate markers in each ring around the circumference to readily discern which marker ring each individually identified marker belongs and hence allow the physician or interventionalist to determine the expansion/crimped state of the device at the discrete location along the length of the device the markers are located.

Figure 13A:
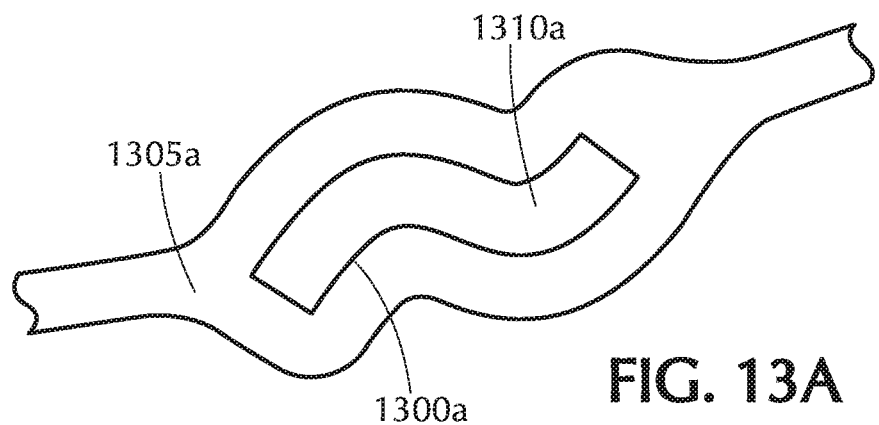
FIG. 13A is a top view of an exemplary S shape eyelet defined in a single strut in accordance with the present invention and a complementary S shape marker rivet secured therein.
Figure 13B:
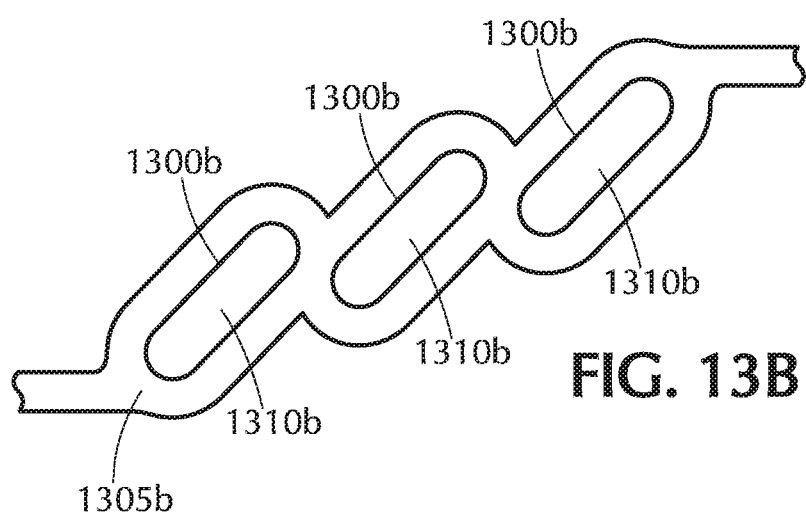
FIG. 13B is a top view of an exemplary single strut in accordance with the present invention having a series of plural eyelets each with an associated marker rivet secured therein, when observed from a side view the non-linearly arranged marker rivets comprising the set overlap each other in series creating a visual effect of a single continuous marker rivet rather than multiple independent marker rivets.

Differentiation or identification of the marker during imaging is achieved, in accordance with the present invention, without increasing overall profile of the mechanical device or negatively impacting its performance (e.g., greater delivery force when advanced through the microcatheter). A top view in FIG. 13A illustrates an assembled S shape eyelet 1300a defined in the strut 1305a with a complementary S shape marker 1310a secured therein. By varying the shape of the individual marker rivet, e.g., lengthening it, the rivet is more pronounced and readily visible during imaging. Alternatively, without increasing the overall profile of the device, the visibility of the marker may be improved by a single crown or single strut (as defined as a segment between adjacent crowns) of the mechanical device having a series of plural markers secured within associated eyelets rather than a single marker secured within a single eyelet. FIG. 13B is a top view of an exemplary single strut, in accordance with the present invention, having a series of plural eyelets each with an associated marker rivet secured therein. When observed from various viewpoints the set of plural markers is more visible than a single marker rivet secured in an associated single eyelet defined in a single strut. For example, when observed from a partial side angled perspective view the series of marker rivets for a single strut overlap each other in series creating a visual effect of a single continuous marker rivet rather than a series of multiple independent, distinct marker rivets using the same overall volume of radiopaque material.

Figure 13C:
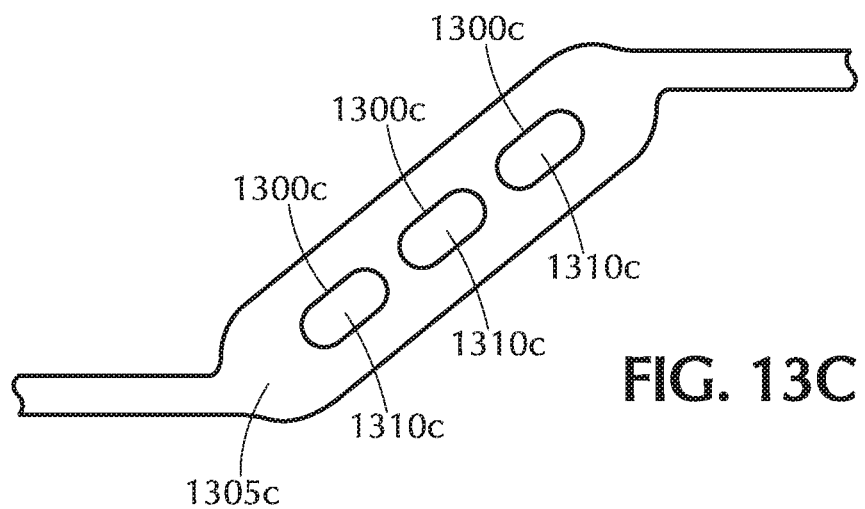
FIG. 13C is a top view of an exemplary single strut in accordance with the present invention having a set of plural eyelets each with an associated marker rivet secured therein, when observed from a side view the marker rivets are arranged linearly in series (without overlap therebetween) producing a more discernible visual observation than produced by a single marker rivet standing alone allowing that particular set to be readily identifiable.

FIG. 13C is a top view of an alternative exemplary single strut, in accordance with the present invention, having a series of plural eyelets linearly arranged each eyelet with an associated marker rivet secured therein. When observed from different viewpoints these set of plural markers are more discernible than a single marker. For instance, when observed from an end or side view, the marker rivets are arranged in linear series (without overlap therebetween) or other uniform configuration producing a more discernible visual observation than produced by a single marker rivet alone in a single eyelet defined in a single strut. Such novel features described in FIGS. 13A-13C may be utilized on any desired strut location (e.g., edge or perimeter) to be readily identifiable and visible during imaging. Despite the fact that each set illustrated in FIGS. 13B & 13C comprises three markers, any number of two or more markers in a series may be used, as desired.

The present inventive features illustrated and described can be use in a mechanical thrombectomy procedure but is also suitable for use in other neurovascular or endovascular medical procedures.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An expandable mechanical device for use during a vascular medical procedure, the device comprising:
    a strut having a top surface, an opposite bottom surface, and an eyelet defined therein by an inner side wall of the strut extending from the top surface to the opposite bottom surface, the eyelet having a geometric shape that includes at least one indent; and
    a marker rivet disposed within the eyelet of the strut, wherein in a pre-crimped state no section of an outer surface of the marker rivet physically contacts the inner side wall of the strut as defined by the eyelet therein; wherein in the post-crimped state the marker rivet forms an overlap area covering the top and bottom surfaces of the strut radially outward relative to the inner side wall of the strut defining the eyelet; and wherein in the pre-crimped state the marker rivet has a geometric shape that includes at least one indent corresponding with the at least one indent of the eyelet of the strut.

2. The expandable mechanical device according to claim 1, wherein the geometric shape of the marker rivet and/or the eyelet includes more than one indent.

3. The expandable mechanical device according to claim 2, wherein the at least one indent of the marker rivet and/or the eyelet comprises indents that are mirror symmetrical images of one another along a longitudinal axis and/or a lateral axis.

4. The expandable mechanical device according to claim 1, wherein the geometric shape of the eyelet is one of a butterfly bandage shape, a rocket shape, or a bow tie shape.

5. The expandable mechanical device according to claim 1, wherein
    along at least one of the top surface top edge or the bottom surface bottom edge of the inner side wall of the strut as defined by the eyelet therein having a chamfer cut.

6. The expandable mechanical device according to claim 5, wherein the chamfer cut is on the top surface top edge of the inner side walls of the strut as defined by the eyelet therein.

7. The expandable mechanical device according to claim 5, wherein the chamfer cut is on the top surface top edge and the bottom surface bottom edge of the inner side walls of the eyelet.

8. The expandable mechanical device according to claim 1, wherein entirely along the outer surface of the marker rivet a gap exists relative to the inner side wall of the strut as defined by the eyelet therein.

* * * * *